US011168000B2

United States Patent
Yakubo

(10) Patent No.: US 11,168,000 B2
(45) Date of Patent: Nov. 9, 2021

(54) METAL OXIDE POWDER, DISPERSION LIQUID, AND COSMETIC MATERIAL

(71) Applicant: SUMITOMO OSAKA CEMENT CO., LTD., Tokyo (JP)

(72) Inventor: Teppei Yakubo, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 0 days.

(21) Appl. No.: 16/066,282

(22) PCT Filed: Dec. 27, 2016

(86) PCT No.: PCT/JP2016/088916
§ 371 (c)(1),
(2) Date: Jun. 26, 2018

(87) PCT Pub. No.: WO2017/115802
PCT Pub. Date: Jul. 6, 2017

(65) Prior Publication Data
US 2019/0016606 A1    Jan. 17, 2019

(30) Foreign Application Priority Data

Dec. 28, 2015 (JP) .............................. JP2015-255773

(51) Int. Cl.
*C01G 23/053* (2006.01)
*A61K 8/29* (2006.01)
(Continued)

(52) U.S. Cl.
CPC ............ *C01G 23/053* (2013.01); *A61K 8/022* (2013.01); *A61K 8/0245* (2013.01); *A61K 8/04* (2013.01);
(Continued)

(58) Field of Classification Search
None
See application file for complete search history.

(56) References Cited

U.S. PATENT DOCUMENTS 5,279,662 A * 1/1994 Smith .................. C09D 17/008
106/436
2010/0150852 A1* 6/2010 Prochazka ............... A61K 8/29
424/59

(Continued)

FOREIGN PATENT DOCUMENTS

JP    2002-293542 A    10/2002
JP    2005-206412 A    8/2005
(Continued)

OTHER PUBLICATIONS

Google Translate. Translation of JP 2009184972 A. Obtained from https://patents.google.com/patent/JP2009184972A/en?oq=JP+2009184972A on Jan. 4, 2019. Document originally published in Japanese on Aug. 20, 2009, pp. 1-7. (Year: 2009).*

(Continued)

*Primary Examiner* — Isaac Shomer
(74) *Attorney, Agent, or Firm* — Merchant & Gould P.C.

(57) ABSTRACT

Metal oxide powder formed of metal oxide particles, in which the metal oxide powder has first metal oxide particles having at least one protrusion portion and second metal oxide particles, the first metal oxide particles have an average primary particle diameter of 100 nm or more and 1,000 nm or less, the second metal oxide particles have an average primary particle diameter of less than 100 nm, and a fraction of a total mass of particles having a primary particle diameter of less than 100 nm in a total mass of the metal oxide powder is 0.3% by mass or more and 10% by mass or less.

7 Claims, 3 Drawing Sheets

(51) Int. Cl.
*A61Q 1/02* (2006.01)
*A61K 8/02* (2006.01)
*A61K 8/04* (2006.01)

(52) U.S. Cl.
CPC ................. *A61K 8/29* (2013.01); *A61Q 1/02* (2013.01); *A61K 2800/412* (2013.01); *A61K 2800/413* (2013.01); *A61K 2800/436* (2013.01); *A61K 2800/61* (2013.01); *A61K 2800/651* (2013.01); *C01P 2004/03* (2013.01); *C01P 2004/45* (2013.01); *C01P 2004/62* (2013.01); *C01P 2004/64* (2013.01)

(56) References Cited

U.S. PATENT DOCUMENTS

| | | | | |
|---|---|---|---|---|
| 2011/0171533 | A1* | 7/2011 | Torardi | B82Y 30/00 429/231.95 |
| 2012/0003287 | A1* | 1/2012 | Schlossman | C09C 1/24 424/401 |
| 2014/0030202 | A1* | 1/2014 | Simonnet | A61Q 19/00 424/63 |
| 2015/0265510 | A1* | 9/2015 | Johncock | A61K 9/5021 424/401 |

FOREIGN PATENT DOCUMENTS

| | | | |
|---|---|---|---|
| JP | 2005232092 | A * | 9/2005 |
| JP | 2005-298316 | A | 10/2005 |
| JP | 2006-076798 | A | 3/2006 |
| JP | 2006076798 | A * | 3/2006 |
| JP | 2007-165508 | A | 6/2007 |
| JP | 2009184972 | A * | 8/2009 |
| JP | 4382607 | A | 12/2009 |
| JP | 4382873 | B1 | 12/2009 |
| JP | 2010001212 | A * | 1/2010 |

OTHER PUBLICATIONS

English Translation of JP 2005232092 A. Accessed at https://patents.google.com/patent/JP2005232092A/en?oq=JP2005-232092 on Nov. 18, 2019. Originally published in Japanese on Sep. 2, 2005. pp. 1/6-6/6. (Year: 2005).*

B Faure et al. "Dispersion and surface functionalization of oxide nanoparticles for transparent photocatalytic and UV-protecting coatings and sunscreens." Science and Technology of Advanced Materials, vol. 14, 2013, pp. 1-23. (Year: 2013).*

English Translation of JP 2006076798 A. Accessed at https://patents.google.com/patent/JP2006076798A/en?oq=JP+2006076798 on Nov. 19, 2019. Originally published in Japanese on Mar. 23, 2006. pp. 1/8-8/8. (Year: 2006).*

English Translation of JP 2010001212 A. Obtained from https://patents.google.com/patent/JP2010001212A/en?oq=JP+4382873 on Nov. 19, 2019. Originally published in Japanese on Jan. 7, 2010. pp. 1/8-8/8. (Year: 2010).*

Chin Xuan Tan. "Virgin avocado oil: An emerging source of functional fruit oil." Journal of Functional Foods 54 (2019) 381-392. (Year: 2019).*

English Translation of tables in Fujihashi et al. (JP 2009-184972 A). Translation obtained by examiner on May 5, 2021, originally published in Japanese on Aug. 20, 2009, 4 printed pages. (Year: 2009).*

International Search Report for PCT/JP2016/088916 (dated Feb. 7, 2017).

Search Report for European Application No. 16881776.5 (dated Jul. 17, 2019).

* cited by examiner

METAL OXIDE POWDER, DISPERSION LIQUID, AND COSMETIC MATERIAL

This application is a U.S. National Stage Application under 35 U.S.C. § 371 of International Patent Application No. PCT/JP2016/088916 filed Dec. 27, 2016, which claims the benefit of priority to Japanese Patent Application No. 2015-255773 filed Dec. 28, 2015 the disclosures of all of which are hereby incorporated by reference in their entireties. The International Application was published in Japanese on Jul. 6, 2017 as WO 2017/115802.

TECHNICAL FIELD

The present invention relates to metal oxide powder, a dispersion liquid, and a cosmetic material.

The present application claims priority on the basis of Japanese Patent Application No. 2015-255773, filed on Dec. 28, 2015, the content of which is incorporated herein.

BACKGROUND

Metal oxide powder formed of metal oxide particles of titanium oxide, zinc oxide, zirconium oxide, or the like has a high refractive index, favorable ultraviolet-shielding properties, and the like and is thus used in a variety of applications. For example, star-like titanium oxide particles described in Patent Literature 1 have a power of scattering visible light through near-infrared light and are included and used in paint, resin compositions, plastic films, plastic plates, and cosmetic materials.

CITATION LIST

Patent Literature

[Patent Literature No. 1] Japanese Patent No. 4382607

SUMMARY OF INVENTION

Technical Problem

However, paint, cosmetic materials, and the like to which the above-described metal oxide powder is added do not have sufficient adhesiveness to substances to be coated.

The present invention has been made to solve the above-described problem, and an object of the present invention is to provide metal oxide powder having excellent light-scattering properties. Furthermore, another object of the present invention is to provide a dispersion liquid and a cosmetic material which include the metal oxide powder, have excellent light-scattering properties, and have excellent adhesiveness to substances to be coated.

Solution to Problem

According to an aspect of the present invention, there is provided metal oxide powder formed of metal oxide particles, in which the metal oxide powder has first metal oxide particles having at least one protrusion portion and second metal oxide particles, the first metal oxide particles have an average primary particle diameter of 100 nm or more and 1,000 nm or less, the second metal oxide particles have an average primary particle diameter of less than 100 nm, and a fraction of a total mass of particles having a primary particle diameter of less than 100 nm in a total mass of the metal oxide powder is 0.3% by mass or more and 10% by mass or less.

In the aspect of the present invention, the first metal oxide particle preferably includes a plurality of first protrusion portions radially protruding from a central axis of the first metal oxide particle in substantially perpendicular directions and a pair of second protrusion portions protruding in a direction in which tips are away from each other along the central axis, has a crest formed between a tip of the first protrusion portion and the tip of the second protrusion portion, and has a star-like shape as a whole.

In the aspect of the present invention, the metal oxide particles are preferably titanium oxide particles.

In the aspect of the present invention, a surface-treated layer formed of a surface treatment agent may be provided on a surface of the metal oxide particle.

According to another aspect of the present invention, there is provided a dispersion liquid including the metal oxide powder and a dispersion medium.

According to still another aspect of the present invention, there is provided a cosmetic material including at least one element selected from the group consisting of the metal oxide powder and the dispersion liquid.

Advantageous Effects of Invention

According to the aspects of the present invention, metal oxide powder having excellent light-scattering properties is provided. Furthermore, a dispersion liquid and a cosmetic material which include the metal oxide powder, have excellent light-scattering properties, and have excellent adhesiveness to substances to be coated are provided.

DESCRIPTION OF EMBODIMENTS

Hereinafter, embodiments of metal oxide powder, a dispersion liquid, and a cosmetic material according to the present invention will be described.

The present embodiments are specific description for better understanding of the gist of the present invention and do not limit the present invention unless particularly otherwise described.

First Embodiment

[Metal Oxide Powder]

Metal oxide powder of the present embodiment is formed of metal oxide particles. The metal oxide powder has first metal oxide particles having at least one protrusion portion and second metal oxide particles. Hereinafter, individual forms of the first metal oxide particle and the second metal oxide particle in the present embodiment will be described in detail with appropriate reference to the accompanying drawings.

As average primary particle diameters that will be used in the following description, values obtained from images obtained using a scanning electron microscope (hereinafter, SEM) in the following manner are employed. The primary particle diameters of individual metal oxide particles in SEM images can be measured using measurement tools such as calipers or image analysis devices.

As the primary particle diameter, a value at which the interval between two parallel lines between which individual metal oxide particles in a SEM image are inserted is maximized (the maximum Feret diameter (JIS Z 8827-1:2008)) is employed. A value obtained by randomly measuring 100 primary particle diameters and averaging the obtained measurement values in a weighted manner is used as the average primary particle diameter.

In a case in which the metal oxide particles form agglomerates (secondary particles), the primary particle diameters of 100 random-selected primary particles constituting the secondary particles are measured, and the average primary particle diameter is obtained.

As the mass of the metal oxide particles, a value obtained in the following manner is employed. First, the primary particle diameters of 100 metal oxide particles randomly selected from an SEM image are measured. Next, the volume of the metal oxide particles is calculated using the primary particle diameters in accordance with the shape of the metal oxide particles. Furthermore, this volume is multiplied by the density of a metal oxide constituting the metal oxide particles, thereby calculating the mass of the metal oxide particles.

(First Metal Oxide Particles)

The first metal oxide particles according to the present embodiment refer to particles having an average primary particle diameter of 100 nm or more and 1,000 nm or less. In this range, the average primary particle diameter of the first metal oxide particles is preferably 150 nm or more and 800 nm or less, more preferably 200 nm or more and 600 nm or less, and still more preferably 250 nm or more and 400 nm or less.

Figure 1:
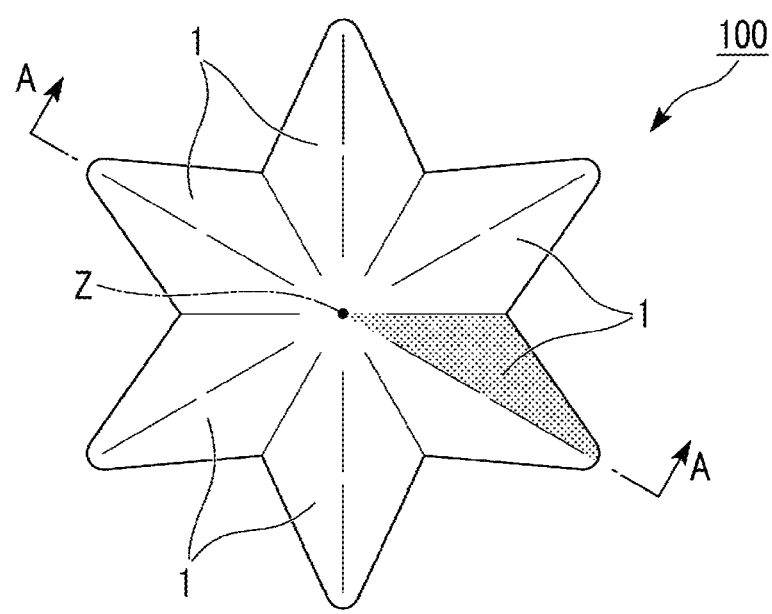
FIG. 1 is a plan view schematically illustrating a first metal oxide particle according to the present embodiment.
Figure 2:
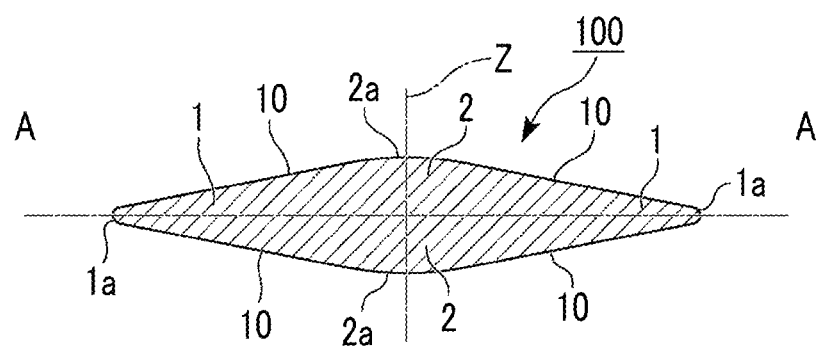
FIG. 2 is a cross-sectional view taken in a direction of an A-A line in FIG. 1.

FIG. 1 is a plan view schematically illustrating a first metal oxide particle 100 according to the present embodiment. FIG. 2 is a cross-sectional view taken in a direction of an A-A line in FIG. 1. The first metal oxide particle 100 illustrated in FIGS. 1 and 2 includes a plurality of first protrusion portions 1 radially protruding from a central axis Z in substantially perpendicular directions to the central axis Z and a pair of second protrusion portions 2 protruding in a direction in which the tips are away from each other along the central axis Z. It is preferable that the first metal oxide particle 100 has a crest 10 formed between a tip 1a of the first protrusion portion 1 and a tip 2a of the second protrusion portion and has a star-like shape as a whole.

In a case in which the first metal oxide particle 100 has a "star-like shape", the first metal oxide particle 100 preferably has six first protrusion portions 1. At this time, the six first protrusion portions 1 are preferably formed at substantially equal intervals in the circumferential direction of the central axis Z.

In FIG. 2, the distance between the two facing tips 2a of the first metal oxide particle 100 having a star-like shape is crystallographically determined by the kind of the metal oxide particle or an exposed crystal plane. For example, in a case in which the metal oxide particle is anatase-type titanium oxide and the principal exposed crystal plane is a (101) plane, the distance is, crystallographically, 0.56 times the primary particle diameter (the distance between the two facing tips 1a). Therefore, in the present embodiment, the distance between the two facing tips 2a of the first metal oxide particle 100 having a star-like shape is considered as a value being crystallographically determined (in a case in which the metal oxide particle is anatase-type titanium oxide and the principal exposed crystal plane is a (101) plane, 0.56 times the primary particle diameter), and the volume of the first metal oxide particle 100 having a star-like shape is calculated.

Figure 3:
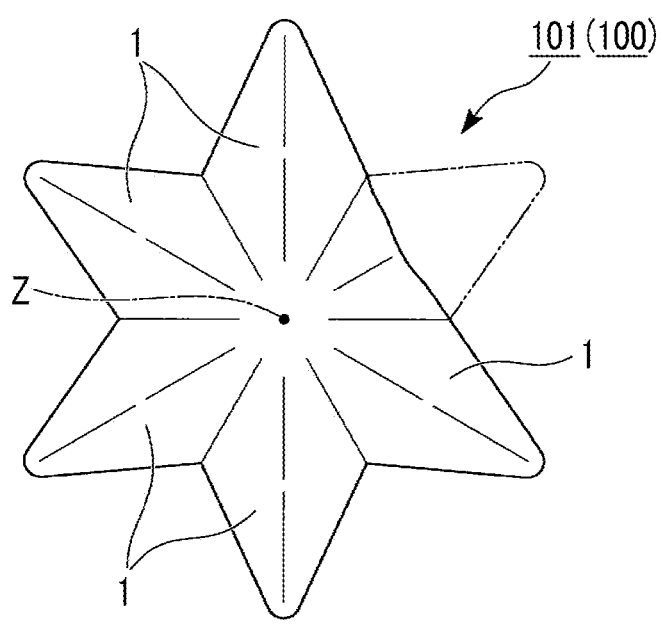
FIG. 3 is a plan view schematically illustrating a modification example of the first metal oxide particle according to the present embodiment.

The first metal oxide particle according to the present embodiment needs to have at least one protrusion portion selected from the group consisting of the first protrusion portions and the second protrusion portions. For example, when the metal oxide particle 101 illustrated in FIG. 3 is compared with the shape of the first metal oxide particle 100 illustrated in FIG. 1, it is possible to assume that one first protrusion portion 1 is broken. In such a case, the first metal oxide particle 101 can be classified as the first metal oxide particle according to the present embodiment. That is, in a case in which a metal oxide particle has a similar shape to the first metal oxide particle 100 illustrated in FIG. 1 and is assumed to be formed from the first metal oxide particle 100 in spite of the broken shape, the metal oxide particle is considered as the first metal oxide particle.

In the first metal oxide particles, the fraction of particles having the above-described star-like shape is preferably 95% by mass or more, more preferably 99% by mass or more, and still more preferably 100% by mass.

In the metal oxide powder of the present embodiment, the second metal oxide particles are preferably present among the first metal oxide particles in a scattered manner. In such a case, a dispersion liquid or a cosmetic material to which the metal oxide powder of the present embodiment is added has excellent adhesiveness to surface to be coated.

The first metal oxide particles according to the present embodiment are preferably formed of, for example, titanium oxide, zinc oxide, zirconium oxide, tin oxide, or the like. The material forming the first metal oxide particles is preferably titanium oxide or zinc oxide since the refractive index is high and the ultraviolet-shielding properties are excellent and more preferably anatase-type titanium oxide since the opacifying power is high and color similar to flesh color is easily obtained.

In the present embodiment, furthermore, anatase-type titanium oxide particles preferably have a principal exposed crystal plane that is a (101) plane. Here, "the principal exposed crystal plane being a (101) plane" means that it is possible to observe the lattice image using a field emission transmission electron microscope (hereinafter, FE-TEM) and determine the exposed crystal plane from the plane spacing and other exposed crystal planes are not substantially observed.

In the present embodiment, in a case in which two or more principal exposed crystal planes are observed when the lattice image is observed using an FE-TEM, the exposed surface is considered to be not determined.

In the present embodiment, an additive may be added to the above-described metal oxide particles as long as the effects of the present invention are not impaired. Examples of the metal oxide particles to which an additive is added include tin oxide particles to which antimony is added and the like. Tin oxide particles to which antimony is added have excellent heat ray-shielding properties.

(Second Metal Oxide Particles)

The second metal oxide particles according to the present embodiment refer to particles having an average primary particle diameter of less than 100 nm. The lower limit value of the average primary particle diameter of the second metal oxide particles according to the present embodiment is not particularly limited, but is preferably 1 nm or more since the second metal oxide particles can be stably manufactured. That is, the average primary particle diameter of the second metal oxide particles according to the present embodiment is 1 nm or more and less than 100 nm, preferably 3 nm or more and 70 nm or less, more preferably 5 nm or more and 50 nm or less, and still more preferably 10 nm or more and 30 nm or less.

The second metal oxide particles according to the present embodiment are preferably formed of, for example, titanium oxide, zinc oxide, zirconium oxide, tin oxide, or the like. The material forming the second metal oxide particles is preferably titanium oxide or zinc oxide since the refractive index is high and the ultraviolet-shielding properties are excellent and more preferably anatase-type titanium oxide since the opacifying power is high and color similar to flesh color is easily obtained.

In the present embodiment, furthermore, anatase-type titanium oxide particles preferably have a principal exposed crystal plane that is a (101) plane. The second metal oxide particles may be formed of the same material as that used to form the first metal oxide particles.

The second metal oxide particles according to the present embodiment are not limited to any specific forms. Examples of the form of the second metal oxide particle include a spherical shape, an elliptical shape, a cuboid shape, a cube shape, a polyhedral shape, a triangular pyramid shape, a square pyramid shape, a spindle shape, a protrusion shape, and a star-like shape. In addition, the second metal oxide particle may be a mixture of metal oxide particles having different forms. The second metal oxide particles preferably have a form including no acute end portions since the adhesion effect can be more easily obtained. Examples of the above-described form include a spherical shape, an elliptical shape, a cuboid shape, a cube shape, and the like.

In a case in which the second metal oxide particle includes metal oxide particles having one or more protrusion portions, for example, includes metal oxide particles having a star-like shape or the like, an embodiment described below is preferred. That is, the fraction of the total mass of the metal oxide particles having one or more protrusion portions which have an average primary particle diameter of less than 100 nm in the total mass of the first metal oxide particles is preferably 0.01% by mass or more and 7% by mass or less, more preferably 0.1% by mass or more and 5% by mass or less, and still more preferably 1.3% by mass or more and 3% by mass or less.

The first metal oxide particles and the second metal oxide particles can be visually differentiated from each other in images obtained using a SEM.

(Content)

The content of the metal oxide particles with respect to the total mass of the metal oxide powder can be measured using an inductively coupled plasma (hereinafter, ICP) emission spectroscopic analysis method.

The total mass of the first metal oxide particles and the second metal oxide particles with respect to the total mass of the metal oxide powder according to the present embodiment is preferably 99.7% by mass or more, more preferably 99.8% by mass or more, and still more preferably 99.9% by mass or more.

For example, when the first metal oxide particles and the second metal oxide particles are titanium oxide particles, the content of the titanium oxide particles in titanium oxide powder is preferably 99.7% by mass or more, more preferably 99.8% by mass or more, and still more preferably 99.9% by mass or more.

Among components included in the metal oxide powder of the present embodiment, examples of components other than the first metal oxide particles and the second metal oxide particles include adsorbed water attached to the metal oxide particles, impurities derived from the raw materials, and the like. In a case in which the metal oxide particles are titanium oxide particles, there are cases in which, for example, iron oxide is included.

The fraction of the total mass of particles having an average primary particle diameter of 100 nm or more and 1,000 nm or less (the first metal oxide particles) in the total mass of the metal oxide powder according to the present embodiment is 90% by mass or more and 99.7% by mass or less, preferably 92% by mass or more and 99.5% by mass or less, more preferably 94% by mass or more and 99.0% by mass or less, and still more preferably 96% by mass or more and 98.5% by mass or less.

The fraction of the total mass of particles having an average primary particle diameter of less than 100 nm (the second metal oxide particles) in the total mass of the metal oxide powder according to the present embodiment is 0.3% by mass or more and 10% by mass or less, preferably 0.5% by mass or more and 8% by mass or less, more preferably 1% by mass or more and 6% by mass or less, and still more preferably 1.5% by mass or more and 4% by mass or less.

When the fraction of the total mass of the particles having a primary particle diameter of less than 100 nm in the total mass of the metal oxide powder satisfies the above-described condition, dispersion liquids or cosmetic materials to which the metal oxide powder of the present embodiment is added exhibits excellent adhesiveness to substances to be coated such as skin.

[Method for Manufacturing Metal Oxide Powder]

A method for manufacturing the metal oxide powder according to the present embodiment is a method for manufacturing the metal oxide powder by preparing the first metal oxide particles and the second metal oxide particles respectively and mixing the particles together. An example of the method for manufacturing the metal oxide powder according to the present embodiment will be described. In the following description, as the first metal oxide particles, star-like titanium oxide particles having an average primary particle diameter of 100 nm or more and 1,000 nm or less are used. In addition, as the second metal oxide particles, anatase-type granular titanium oxide particles having an average primary particle diameter of 1 nm or more and 40 nm or less are used.

(Method for Manufacturing Anatase-Type Star-Like Titanium Oxide Particles)

The star-like titanium oxide particles having an average primary particle diameter of 100 nm or more and 1,000 nm or less can be manufactured using a well-known method. Examples of the well-known method include the manufacturing method described in Japanese Laid-open Patent Publication No. 2009-292717. Specifically, the above-described star-like titanium oxide particles can be manufactured by mixing a hydrolysis product of a titanium alkoxide or a titanium metal salt and an organic alkali in a predetermined solvent and reacting the obtained reaction solution in the presence of high-temperature and high-pressure hot water (hydrothermal synthesis).

Examples of the titanium alkoxide in the present embodiment include titanium ethoxide, titanium tetraisopropoxide, titanium n-propoxide, titanium tetrabutoxide, and the like. The titanium alkoxide is preferably titanium tetraisopropoxide and titanium tetrabutoxide and more preferably titanium tetraisopropoxide since it is easy to procure these titanim alkoxides and control the hydrolysis rates.

Examples of the titanium metal salt in the present embodiment include titanium tetrachloride, titanium sulfate, and the like.

In the present embodiment, in order to obtain high-purity star-like titanium oxide particles, a high-purity titanium alkoxide or a high-purity titanium metal salt is preferably used.

The hydrolysis product in the present embodiment is obtained by hydrolyzing the above-described titanium alkoxide or titanium metal salt. The hydrolysis product being obtained is, for example, a cake-form solid and is water-containing titanium oxide called metatitanic acid or orthotitanic acid.

The hydrolysis product obtained by hydrolyzing the titanium alkoxide or titanium metal salt includes alcohols, hydrochloric acid, and sulfuric acid which are by-products. These substances hinder the crystal growth of the titanium oxide particles and are thus preferably cleaned with pure water. A method for cleaning the hydrolysis product is preferably, for example, decantation, the Nutsche method, or ultrafiltration.

The organic alkalis in the present embodiment have a function as a pH adjuster for the reaction solution and a function as a catalyst for hydrothermal synthesis described below. Examples of the organic alkalis include amines, high-molecular-weight amines, salts of high-molecular-weight amines, compounds having a five-membered ring including ammonia or nitrogen, and the like.

Examples of the amines include tetramethylammonium hydroxide, tetraethylammonium hydroxide, tetrapropylammonium hydroxide, tetrabutylammonium hydroxide, monoethanolamine, diethanolamine, triethanolamine, tetramethylammonium chloride, tetraethylammonium chloride, tetrapropylammonium chloride, tetrabutylammonium chloride, octylamine, laurylamine, stearylamine, and the like.

Examples of the high-molecular-weight amines and the salts of high-molecular-weight amines include high-molecular-weight amines and salts of high-molecular-weight amines which are made of the above-described amines.

Examples of the compounds having a five-membered ring including nitrogen include pyrrol, imidazole, indole, purine, pyrrolidine, pyrazole, triazole, tetrazole, isothiazole, isooxazole, furazan, carbazole, 1,5-diasabicyclo-[4.3.0]-5-nonene, and the like.

Among the compounds having a five-membered ring including nitrogen, compounds having a five-membered ring including one nitrogen atom are preferred since the particle size distribution is narrow and thus titanium oxide particles having excellent crystallinity can be manufactured. Examples thereof include pyrrol, indole, pyrrolidine, isothiazole, isooxazole, furazan, carbazole, 1,5-diasabicyclo-[4.3.0]-5-nonene, and the like.

Furthermore, among the compounds having a five-membered ring including one nitrogen atom, compounds in which the five-membered ring has a saturated heterocyclic structure are more preferred since the particle size distribution is narrower than those of the above-described compounds and titanium oxide particles having excellent crystallinity can be manufactured. Examples thereof include pyrrolidine, 1,5-diasabicyclo-[4.3.0]-5-nonene, and the like.

When these compounds having a five-membered ring including nitrogen are used as a catalyst for hydrothermal synthesis, anatase single-phase (anatase-type) star-like titanium oxide particles, in which a principal exposed crystal plane is a (101) plane, can be obtained.

In the present embodiment, the amount of the organic alkali blended is preferably 0.008 mol to 0.09 mol, more preferably 0.009 mol to 0.08 mol, and still more preferably 0.01 mol to 0.07 mol with respect to 1 mol of titanium atoms in the hydrolysis product.

The reaction solution in the present embodiment is obtained by mixing the hydrolysis product of the titanium alkoxide or the titanium metal salt and the organic alkali in a predetermined solvent. A method for producing this reaction solution is not particularly limited as long as the above-described components can be uniformly dispersed. Examples of the method for producing the reaction solution include methods in which the hydrolysis product and the organic alkali are mixed together using a stirrer, a beads mill, a ball mill, an attritor, a dissolver, or the like.

In addition, in the present embodiment, it is also possible to add water to the reaction solution and adjust the concentration of the reaction solution. Examples of water being added to the reaction solution include deionized water, distilled water, pure water, and the like.

The pH of the solution after a hydrothermal reaction according to the present embodiment is preferably 9 to 12.5 and more preferably 10 to 12. In the embodiment, the pH of the solution after the hydrothermal reaction can be adjusted to the above-described range by controlling the amount of the organic alkali blended.

In the present embodiment, when the pH of the solution after the hydrothermal reaction is lower than 9, there are cases in which the catalytic action of the organic alkali for the formation of nuclei weakens. In such a case, the nucleation rate of titanium oxide particles being generated in the reaction solution becomes slow, and there are cases in which the number of nuclei of titanium oxide particles in the reaction solution decreases. Therefore, there are cases in which the primary particle diameters of the respective titanium oxide particles become large and the average primary particle diameter of titanium oxide particles being obtained becomes too large.

On the other hand, when the pH of the solution after the hydrothermal reaction is higher than 12.5, the nucleation rate of titanium oxide particles being generated in the reaction solution becomes fast, and there are cases in which the number of nuclei of titanium oxide particles in the reaction solution increases. Therefore, there are cases in which the primary particle diameters of the respective titanium oxide particles become small and the average primary particle diameter of titanium oxide particles being obtained becomes too small.

In the present embodiment, the shape, average primary particle diameter, and particle size distribution of star-like titanium oxide particles being obtained can be controlled by adjusting the pH of the reaction solution.

The concentration of titanium atoms in the reaction solution according to the present embodiment can be appropriately set in accordance with the desired average primary particle diameter of titanium oxide particles. The concentration of the titanium atoms in the reaction solution is preferably 0.05 mol/L to 3.0 mol/L and more preferably 0.1 mol/L to 2.5 mol/L. In the present embodiment, the concentration of the titanium atoms in the reaction solution can be controlled in the above-described range by controlling the content of the hydrolysis product of the titanium alkoxide or the titanium metal salt.

In the present embodiment, when the concentration of the titanium atoms in the reaction solution is lower than 0.05 mol/L, the nucleation rate of titanium oxide particles being generated in the reaction solution becomes slow, and there are cases in which the number of nuclei of titanium oxide particles in the reaction solution decreases. Therefore, there are cases in which the primary particle diameters of the respective titanium oxide particles become large and the average primary particle diameter of titanium oxide particles being obtained becomes too large.

On the other hand, when the concentration of the titanium atoms in the reaction solution is higher than 3.0 mol/L, the nucleation rate of titanium oxide particles being generated in the reaction solution becomes fast, and there are cases in which the number of nuclei of titanium oxide particles in the reaction solution increases. Therefore, there are cases in which the primary particle diameters of the respective titanium oxide particles become small and the average primary particle diameter of titanium oxide particles being obtained becomes too small.

In the present embodiment, the molar ratio between the titanium atoms and the organic alkali in the reaction solution is preferably in a range of 1.00:0.008 to 1.00:0.09 and more preferably in a range of 1.00:0.009 to 1.00:0.08. When the molar ratio between the titanium atoms and the organic alkali in the reaction solution is in the above-described range, titanium oxide particles having excellent crystallinity can be synthesized.

In the present embodiment, star-like titanium oxide particles can be manufactured by reacting the above-described reaction solution in the presence of high-temperature and high-pressure hot water. Synthesis in which the reaction solution is reacted in the presence of high-temperature and high-pressure hot water is referred to as hydrothermal synthesis. In the hydrothermal synthesis of the present embodiment, a sealable high-temperature and high-pressure container (autoclave) is preferably used.

The heating temperature in the hydrothermal synthesis in the present embodiment is preferably 150° C. to 350° C. and more preferably 200° C. to 350° C. In the present embodiment, the heating rate from room temperature to the above-described temperature range is not particularly limited. In addition, the pressure in the hydrothermal synthesis in the present embodiment is set to a pressure at which the reaction solution is heated to the above-described temperature range in the sealed container.

When the heating temperature in the hydrothermal synthesis is in the above-described range, the solubility of the hydrolysis product of the titanium alkoxide or the titanium metal salt in water improves, and it is possible to dissolve the hydrolysis product in the reaction solution. Furthermore, when the heating temperature in the hydrothermal synthesis is in the above-described range, it is possible to generate the nuclei of the titanium oxide particles and grow the nuclei. Therefore, it is possible to manufacture desired star-like titanium oxide particles.

The heating time in the hydrothermal synthesis in the present embodiment needs to be appropriately adjusted so that the metal oxide particles become as large as desired and is preferably two hours or longer and more preferably three hours or longer. When the heating time is shorter than two hours, there are cases in which the raw material (the hydrolysis product of the titanium alkoxide or the titanium metal salt) is not consumed and the yield deceases. Since the heating time is influenced by the kind or concentration of the raw material, the heating time needs to be set so that the metal oxide particles become as large as desired by means of appropriate preliminary tests. For example, the heating time may be nine hours, 12 hours, 24 hours, 48 hours, or 72 hours. The heating may be stopped when the metal oxide particles have become as large as desired from the viewpoint of production efficiency.

In the hydrothermal synthesis in the present embodiment, it is preferable to carry out preliminary heating (the preheating of the reaction solution at a temperature lower than the above-described temperature range). When the preliminary heating is carried out in a temperature range of 70° C. to 150° C. for one hour or longer, only star-like titanium oxide particles having an average primary particle diameter of 100 nm or more and 1,000 nm or less are formed. In contrast, when the preliminary heating is not carried out, granular titanium oxide particles having an average primary particle diameter of 1 nm or more and 40 nm or less as well as star-like titanium oxide particles having an average primary particle diameter of 100 nm or more and 1,000 nm or less are formed.

In the present embodiment, examples of a method for extracting the star-like titanium oxide particles from the reaction solution include methods for separating solid and liquid using decantation, the Nutsche method, or the like. After the star-like titanium oxide particles are extracted, the obtained star-like titanium oxide particles may be cleaned with pure water or the like for the purpose of reducing impurities.

When the extracted star-like titanium oxide particles are dried using a well-known method, desired star-like titanium oxide particles can be obtained.

In the present embodiment, solutions including the hydrolysis product of the titanium alkoxide or the titanium metal salt or the reaction solution is preferably forcibly stirred using a stirring device such as a stirrer or a stirring blade. The stirring rate in the present invention is preferably, for example, 100 rpm to 300 rpm.

(Method for Manufacturing Anatase-Type Granular Titanium Oxide Particles)

Anatase-type granular titanium oxide particles can be manufactured using a well-known method. Examples of the well-known method include the manufacturing method described in Japanese Laid-open Patent Publication No. 2007-176753. Specifically, the above-described titanium oxide particles can be manufactured by using the hydrolysis product of the titanium alkoxide or the titanium metal salt as a starting material and crystallizing a mixture of the hydrolysis product and an alkali aqueous solution, water, a diol, or a triol.

In addition, as another method, the anatase-type granular titanium oxide particles can be manufactured by producing a reaction solution by mixing the hydrolysis product of the titanium alkoxide or the titanium metal salt and the compound having a five-membered ring including nitrogen and reacting the reaction solution in the presence of high-temperature and high-pressure hot water (hydrothermal synthesis).

Examples of the titanium alkoxide in the present embodiment include titanium ethoxide, titanium tetraisopropoxide, titanium n-propoxide, titanium tetrabutoxide, and the like. The titanium alkoxide is preferably titanium tetraisopropoxide and titanium tetrabutoxide and more preferably titanium tetraisopropoxide since it is easy to procure these titanim alkoxides and control the hydrolysis rates.

Examples of the titanium metal salt in the present embodiment include titanium tetrachloride, titanium sulfate, and the like.

In the present embodiment, in order to obtain high-purity anatase-type granular titanium oxide particles, a high-purity titanium alkoxide or a high-purity titanium metal salt is preferably used.

The hydrolysis product in the present embodiment is obtained by hydrolyzing the above-described titanium alkoxide or titanium metal salt. The hydrolysis product being obtained is, for example, a cake-form solid and is water-containing titanium oxide called metatitanic acid or orthotitanic acid.

The hydrolysis product obtained by hydrolyzing the titanium alkoxide or titanium metal salt includes alcohols, hydrochloric acid, and sulfuric acid which are by-products. These substances hinder the crystal growth of the titanium oxide particles and are thus preferably cleaned with pure water. A method for cleaning the hydrolysis product is preferably, for example, decantation, the Nutsche method, or ultrafiltration.

The compound having a five-membered ring including nitrogen in the present embodiment has a function as a pH adjuster for the reaction solution and a function as a catalyst for hydrothermal synthesis described below. Examples of the compound having a five-membered ring including nitrogen include pyrrol, imidazole, indole, purine, pyrrolidine, pyrazole, triazole, tetrazole, isothiazole, isooxazole, furazan, carbazole, 1,5-diasabicyclo-[4.3.0]-5-nonene, and the like.

Among the compounds having a five-membered ring including nitrogen, compounds having a five-membered ring including one nitrogen atom are preferred since the particle size distribution is narrow and thus titanium oxide particles having excellent crystallinity can be manufactured. Examples thereof include pyrrol, indole, pyrrolidine, isothiazole, isooxazole, furazan, carbazole, 1,5-diasabicyclo-[4.3.0]-5-nonene, and the like.

Furthermore, among the compounds having a five-membered ring including one nitrogen atom, compounds in which the five-membered ring has a saturated heterocyclic structure are more preferred since the particle size distribution is narrower than those of the above-described compounds and titanium oxide particles having excellent crystallinity can be manufactured. Examples thereof include pyrrolidine, 1,5-diasabicyclo-[4.3.0]-5-nonene, and the like.

When these compounds having a five-membered ring including nitrogen are used as a catalyst for hydrothermal synthesis, anatase single-phase (anatase-type) granular titanium oxide particles, in which a principal exposed crystal plane is a (101) plane, can be obtained.

In the present embodiment, the amount of the compound having a five-membered ring including nitrogen blended is preferably 0.1 mol to 1.0 mol, more preferably 0.1 mol to 0.7 mol, and still more preferably 0.1 mol to 0.5 mol with respect to 1 mol of titanium atoms in the hydrolysis product.

The reaction solution in the present embodiment is obtained by mixing the hydrolysis product of the titanium alkoxide or the titanium metal salt and the compound having a five-membered ring including nitrogen. A method for producing this reaction solution is not particularly limited as long as the above-described components can be uniformly dispersed. Examples of the method for producing the reaction solution include methods in which the hydrolysis product and the compound having a five-membered ring including nitrogen are mixed together using a stirrer, a beads mill, a ball mill, an attritor, a dissolver, or the like.

In addition, in the present embodiment, it is also possible to add water to the reaction solution and adjust the concentration of the reaction solution. Examples of water being added to the reaction solution include deionized water, distilled water, pure water, and the like.

The pH of the solution after the hydrothermal synthesis according to the present embodiment is preferably 9 to 13 and more preferably 11 to 13. In the embodiment, the pH of the solution after the hydrothermal synthesis can be adjusted to the above-described range by controlling the amount of the compound having a five-membered ring including nitrogen blended.

In the present embodiment, when the pH of the solution after the hydrothermal synthesis is lower than 9, there are cases in which the catalytic action of the compound having a five-membered ring including nitrogen for the formation of nuclei weakens. In such a case, the nucleation rate of titanium oxide particles being generated in the reaction solution becomes slow, and there are cases in which the number of nuclei of titanium oxide particles in the reaction solution decreases. Therefore, there are cases in which the primary particle diameters of the respective titanium oxide particles become large and the average primary particle diameter of titanium oxide particles being obtained becomes too large.

On the other hand, when the pH of the solution after the hydrothermal reaction is higher than 13, the nucleation rate of titanium oxide particles being generated in the reaction solution becomes fast, and there are cases in which the number of nuclei of titanium oxide particles in the reaction solution increases. Therefore, there are cases in which the primary particle diameters of the respective titanium oxide particles become small and the average primary particle diameter of titanium oxide particles being obtained becomes too small.

In addition, when the pH of the solution after the hydrothermal synthesis is higher than 13, there are cases in which the dispersibility of the reaction solution varies and the particle size distribution of titanium oxide particles being generated becomes too wide.

In the present embodiment, the shape, average primary particle diameter, and particle size distribution of anatase-type granular titanium oxide particles being obtained can be controlled by adjusting the pH of the reaction solution.

The concentration of titanium atoms in the reaction solution according to the present embodiment can be appropriately set in accordance with the desired average primary particle diameter of titanium oxide particles. The concentration of the titanium atoms in the reaction solution is preferably 0.05 mol/L to 3.0 mol/L and more preferably 0.5 mol/L to 2.5 mol/L. In the present embodiment, the concentration of the titanium atoms in the reaction solution can be controlled in the above-described range by controlling the content of the hydrolysis product of the titanium alkoxide or the titanium metal salt.

In the present embodiment, when the concentration of the titanium atoms in the reaction solution is lower than 0.05 mol/L, the nucleation rate of titanium oxide particles being generated in the reaction solution becomes slow, and there are cases in which the number of nuclei of titanium oxide particles in the reaction solution decreases. Therefore, there are cases in which the primary particle diameters of the respective titanium oxide particles become large and the average primary particle diameter of titanium oxide particles being obtained becomes too large.

On the other hand, when the concentration of the titanium atoms in the reaction solution is higher than 3.0 mol/L, the nucleation rate of titanium oxide particles being generated in the reaction solution becomes fast, and there are cases in which the number of nuclei of titanium oxide particles in the reaction solution increases. Therefore, there are cases in which the primary particle diameters of the respective titanium oxide particles become small and the average primary particle diameter of titanium oxide particles being obtained becomes too small.

In addition, when the concentration of the titanium atoms in the reaction solution is higher than 3.0 mol/L, there are cases in which the dispersibility of the reaction solution varies and the particle size distribution of titanium oxide particles being generated becomes too wide.

In the present embodiment, the molar ratio between the titanium atoms and the compound having a five-membered ring including nitrogen in the reaction solution is preferably in a range of 1.00:0.10 to 1.00:1.00 and more preferably in a range of 1.00:0.10 to 1.00:0.70. When the molar ratio between the titanium atoms and the compound having a five-membered ring including nitrogen in the reaction solution is in the above-described range, titanium oxide particles having excellent crystallinity can be synthesized.

In the present embodiment, anatase-type granular titanium oxide particles can be manufactured by reacting the above-described reaction solution in the presence of high-temperature and high-pressure hot water. Synthesis in which the reaction solution is reacted in the presence of high-temperature and high-pressure hot water is referred to as hydrothermal synthesis. In the hydrothermal synthesis of the present embodiment, a sealable high-temperature and high-pressure container (autoclave) is preferably used.

The heating temperature in the hydrothermal synthesis in the present embodiment is preferably 150° C. to 350° C. and more preferably 150° C. to 210° C. In the present embodiment, the heating rate from room temperature to the above-described temperature range is not particularly limited. In addition, the pressure in the hydrothermal synthesis in the present embodiment is set to a pressure at which the reaction solution is heated to the above-described temperature range in the sealed container.

When the heating temperature in the hydrothermal synthesis is in the above-described range, the solubility of the hydrolysis product of the titanium alkoxide or the titanium metal salt in water improves, and it is possible to dissolve the hydrolysis product in the reaction solution. Furthermore, when the heating temperature in the hydrothermal synthesis is in the above-described range, it is possible to generate the nuclei of the titanium oxide particles and grow the nuclei. Therefore, it is possible to manufacture desired anatase-type granular titanium oxide particles.

The heating time in the hydrothermal synthesis in the present embodiment needs to be appropriately adjusted so that the metal oxide particles become as large as desired and is preferably three hours or longer and more preferably four hours or longer.

When the heating time is shorter than three hours, there are cases in which the raw material (the hydrolysis product of the titanium alkoxide or the titanium metal salt) is not consumed and the yield deceases. Since the heating time is influenced by the kind or concentration of the raw material, the heating time needs to be set so that the metal oxide particles become as large as desired by means of appropriate preliminary tests. For example, the heating time may be nine hours, 12 hours, 24 hours, 48 hours, or 72 hours. The heating may be stopped when the metal oxide particles have become as large as desired from the viewpoint of production efficiency.

In the present embodiment, examples of a method for extracting the anatase-type granular titanium oxide particles from the reaction solution include methods for separating solid and liquid using decantation, the Nutsche method, or the like. After the anatase-type granular titanium oxide particles are extracted, the obtained granular titanium oxide particles may be cleaned with pure water or the like for the purpose of reducing impurities.

When the extracted anatase-type granular titanium oxide particles are dried using a well-known method, desired anatase-type granular titanium oxide particles can be obtained.

In the present embodiment, solutions including the hydrolysis product of the titanium alkoxide or the titanium metal salt or the reaction solution is preferably forcibly stirred using a stirring device such as a stirrer or a stirring blade. The stirring rate in the present invention is preferably, for example, 100 rpm to 300 rpm.

(Method for Manufacturing Metal Oxide Powder)

A method for mixing the first metal oxide particles and the second metal oxide particles is not particularly limited, and examples thereof include methods in which the metal oxide particles are mixed together using a well-known tool or device. Examples of the well-known tool include a mortar and the like. Examples of the well-known device include a mixer, a ball mill, and the like.

According to the present embodiment, it is possible to obtain metal oxide powder which has excellent light-scattering properties and provides dispersion liquids or cosmetic materials with excellent adhesiveness to substances to be coated (surfaces to be coated) when included in the dispersion liquids or the cosmetic materials.

[Surface Treatment]

In the present embodiment, a surface-treated layer formed of a surface treatment agent may be provided on the surface of the metal oxide particle.

The above-described surface treatment agent is not particularly limited and can be appropriately selected in accordance with the applications of the metal oxide powder. Hereinafter, an example of the surface treatment agent according to the present embodiment will be described by showing a case in which the metal oxide powder of the present embodiment is included in a cosmetic material, but the surface treatment agent according to the present embodiment is not limited thereto.

The surface treatment agent in the present embodiment is not particularly limited as long as the surface treatment agent is a surface treatment agent that has been used for cosmetic materials in the related art, and any one of an inorganic component or an organic component can be used.

Examples of the inorganic component include silica, alumina, and the like, and examples of the organic component include at least one component selected from the group consisting of silicone compounds, organopolysiloxanes, fatty acids, fatty acid soap, fatty acid esters, and organic titanate compounds.

In addition, as the inorganic component or the organic component, a surfactant may be used.

Examples of the silicone compounds include silicone oil such as methyl hydrogen polysiloxane, dimethyl polysiloxane, and methyl phenyl polysiloxane, alkyl silanes such as methyltrimethoxysilane, ethyltrimethoxysilane, hexyltrimethoxysilane, and octyltrimethoxysilane, fluoroalkyl silanes such as trifluoromethylethyltrimethoxysilane, heptadecafluorodecyltrimethoxysilane, methicone, hydrogen dimethicone, triethoxysilylethyl polydimethylsiloxyethyl dimethicone, triethoxysilylethyl polydimethylsiloxyethyl hexyl dimethicone, (acrylate/tridecyl acrylate/triethoxysilylpropyl methacrylate/dimethicone methacrylate) copolymers, triethoxycaprylylsilane, and the like. In addition, as the silicone compounds, copolymers of these silicone compounds may be used.

These silicone compounds may be used singly, or a combination of two or more silicone compounds may be used.

Examples of the fatty acids include palmitic acid, isostearic acid, stearic acid, lauric acid, myristic acid, behenic acid, oleic acid, rosin acids, 12-hydroxystearic acid, and the like.

Examples of the fatty acid soap include aluminum stearate, calcium stearate, aluminum 12-hydroxystearate, and the like.

Examples of the fatty acid esters include dextrin fatty acid ester, cholesterol fatty acid ester, sucrose fatty acid ester, starch fatty acid ester, and the like.

Examples of the organic titanate compounds include isopropyl triisostearoyl titanate, isopropyl dimethacryl isostearoyl titanate, isopropyl tri(dodecyl)benzene sulfonyl titanate, neopentyl (diallyl)oxy-tri(dioctyl)phosphate titanate, neopentyl (diallyl)oxy-trineododecanoyl titanate, and the like.

As described above, an example of the surface treatment agent according to the present embodiment has been described by showing a case in which the metal oxide powder of the present embodiment is included in a cosmetic material. In a case in which the metal oxide powder of the present embodiment is included in ultraviolet-shielding films, gas-barrier films, or the like, it is also possible to use an ordinary dispersant in addition to the above-described surface treatment agent. Examples of the ordinary dispersant include anionic dispersants, cationic dispersants, nonionic dispersants, silane coupling agents, wet dispersants, and the like.

A method for forming the surface-treated layer formed of the surface treatment agent on the surface of the metal oxide particle according to the present embodiment is not particularly limited, and well-known methods can be employed in accordance with the kind of the surface treatment agent.

According to the present embodiment, it is possible to obtain metal oxide powder having excellent light-scattering properties. In addition, when the metal oxide powder is surface-treated using the above-described surface treatment agent, it is possible to suppress the surface activity of the metal oxide powder and improve the dispersibility.

[Dispersion Liquid]

A dispersion liquid of the present embodiment includes the above-described metal oxide powder and a dispersion medium. The dispersion liquid of the present embodiment also includes a paste-form dispersion element having a high viscosity.

A dispersion medium that is included in the dispersion liquid of the present embodiment can be appropriately selected depending on the applications of the dispersion liquid. Hereinafter, an example of the dispersion medium according to the present embodiment will be described, but the dispersion medium in the present embodiment is not limited thereto.

Examples of the dispersion medium according to the present embodiment include alcohols, esters, ethers, ketones, hydrocarbons, amides, polysiloxanes, and modified bodies of polysiloxanes.

The alcohols are preferably, for example, water, methanol, ethanol, 1-propanol, 2-propanol, 1-butanol, 2-butanol, octanol, glycerin, or the like.

The esters are preferably, for example, ethyl acetate, butyl acetate, ethyl lactate, propylene glycol monomethyl ether acetate, propylene glycol monoethyl ether acetate, γ-butyrolactone, or the like.

The ethers are preferably, for example, diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, diethylene glycol monoethyl ether, or the like.

The ketones are preferably, for example, acetone, methyl ethyl ketone, methyl isobutyl ketone, acetylacetone, cyclohexanone, and the like.

The hydrocarbons are preferably, for example, aromatic hydrocarbons such as benzene, toluene, xylene, and ethylbenzene or cyclic hydrocarbons such as cyclohexane.

The amides are preferably, for example, dimethylformamide, N,N-dimethylacetoacetamide, N-methyl pyrrolidone, or the like.

The polysiloxanes are preferably, for example, chain-like polysiloxanes such as dimethyl polysiloxane, methyl phenyl polysiloxane, and diphenyl polysiloxane, cyclic polysiloxanes such as octamethylcyclotetrasiloxane, decamethylcyclopentasiloxane, and dodecamethylcyclohexanesiloxane.

The modified bodies of polysiloxanes are preferably, for example, amino-modified polysiloxanes, polyether-modified polysiloxanes, alkyl-modified polysiloxanes, fluorine-modified polysiloxanes, or the like.

In addition, as additional dispersion media, hydrophobic dispersion media such as hydrocarbon oils such as liquid paraffin, squalane, isoparaffin, branched chain-like light paraffin, vaseline, and ceresin, ester oils such as isopropyl myristate, cetylisooctanoate, and glyceryl trioctanoate, silicone oils such as decamethylcyclopentasiloxane, dimethylpolysiloxane, and methyl phenyl polysiloxane, high fatty acids such as lauric acid, myristic acid, palmitic acid, and stearic acid, and higher alcohols such as lauryl alcohol, cetyl alcohol, stearyl alcohol, hexyl dodecanol, isostaryl alcohol may be used.

Only one dispersion medium of the present embodiment may be used singly, or a mixture of two or more dispersion media may also be used.

The content of the dispersion medium included in the dispersion liquid of the present embodiment can be appropriately adjusted in accordance with the applications of the dispersion liquid. The content of the dispersion medium with respect to the mass of the dispersion liquid is, for example, preferably 10% by mass or more and 99% by mass or less, more preferably 20% by mass or more and 90% by mass or less, and still more preferably 30% by mass or more and 80% by mass or less.

The dispersion liquid of the present embodiment may include an additive that is generally used in dispersion liquids as long as the effects of the present invention are not impaired. Examples of the above-described additive include a dispersant, a stabilizer, a water-soluble binder, a viscosity improver, an oil-soluble preservative, an ultraviolet absorbent, an oil-soluble medicinal agent, oil-soluble dyes, oil-soluble proteins, plant oil, animal oil, and the like.

A method for manufacturing the dispersion liquid according to the present embodiment is not particularly limited, and well-known methods can be employed. For example, the dispersion liquid can be obtained by mechanically dispersing the metal oxide powder of the present embodiment with respect to the dispersion medium using a dispersion device.

Examples of the above-described dispersion device include a stirrer, a rotation and revolution-type mixer, a homo mixer, an ultrasonic homogenizer, a sand mill, a ball mill, a roll mill, and the like.

According to the present embodiment, it is possible to obtain a dispersion liquid having excellent light-scattering properties and excellent adhesiveness to substances to be coated.

[Cosmetic Material]

A cosmetic material of the present embodiment includes at least one element selected from the group consisting of the above-described metal oxide powder and dispersion liquid.

A cosmetic material of another embodiment includes a cosmetic vehicle raw material and at least one element selected from the group consisting of metal oxide powder of the present embodiment and the dispersion liquid of the present embodiment.

[Cosmetic material]

A cosmetic material of the present embodiment includes at least one element selected from the group consisting of the above-described metal oxide powder and dispersion liquid.

A cosmetic material of another embodiment includes a cosmetic vehicle raw material and at least one element selected from the group consisting of metal oxide powder of the present embodiment and the dispersion liquid of the present embodiment.

The cosmetic vehicle raw material refers to a variety of raw materials that form the main body of cosmetic products, and examples thereof include oil-based raw materials, water-based raw materials, a surfactant, powder raw materials, and the like.

Examples of the oil-based raw materials include fats, higher fatty acids, higher alcohols, ester oils, and the like.

Examples of the water-based raw materials include purified water, alcohols, viscosity improvers, and the like. Examples of the powder raw materials include color pigments, white pigments, pearl agents, body pigments, and the like.

At least one component selected from the group consisting of the metal oxide powder and the dispersion liquid of the present embodiment is used by being blended into well-known cosmetic materials of the related art. The amount of the component blended is preferably in a range of 0.1% to 50% by mass of the mass of the cosmetic material.

A method for blending the cosmetic material according to the present embodiment is not particularly limited, and well-known methods can be employed. For example, at least one element selected from the group consisting of the metal oxide powder and the dispersion liquid may be blended into the cosmetic vehicle raw material in advance and then other cosmetic material components may be blended thereinto or the element may be blended into the existing cosmetic materials afterwards.

Examples of the cosmetic material of the present embodiment include skin lotions, emulsions, creams, ointments, foundation, lip balms, lipsticks, mascara, eye shadows, eyebrow pencils, nail enamel, cheek colors, and the like.

The cosmetic material of the present embodiment may be appropriately selected in accordance with the characteristics of the metal oxide powder. For example, titanium oxide powder has ultraviolet-shielding properties and hiding characteristics that hide melasma, wrinkles, and the like and is thus preferably used in makeup cosmetic materials for foundation and the like. As a material forming this titanium oxide powder, anatase-type titanium oxide particles are preferably used, and anatase-type titanium oxide particles having a principal exposed crystal plane in a (101) plane is more preferably used since the particles have a color hue close to flesh color.

Here, as the principal exposed crystal plane of the metal oxide particles, a value obtained in the following manner is employed. The lattice image of the metal oxide particles is observed using an FE-TEM, and the exposed crystal plane is determined from the plane spacing. At this time, in a case in which two or more principal exposed crystal planes are observed, the exposed surface is considered to be not determined.

The form of the cosmetic material according to the present embodiment is not particularly limited, and examples thereof include a solid form, a liquid form, a gel form, and the like. In addition, in a case in which the form of the cosmetic material is a liquid form or a gel form, the dispersion form of the cosmetic material is also not particularly limited, and any one of water-in-oil-type (W/O-type) emulsions, oil-in-water-type (O/W-type) emulsions, an oil type, a water type, and the like can be selected.

Into the cosmetic material of the present embodiment, in addition to the above-described metal oxide powder, well-known components that have been used in cosmetic materials in the related art may be blended as long as the effects of the present invention are not impaired. Examples of the well-known components include a solvent, an oil solution, a surfactant, a moisturizer, an organic ultraviolet absorbent, an antioxidant, a viscosity improver, a perfume, a colorant, bioactive components, an antibacterial agent, and the like.

According to the present embodiment, it is possible to obtain a cosmetic material having excellent light-scattering properties and excellent adhesiveness to substances to be coated.

Second Embodiment

A difference between the first embodiment and a second embodiment of the present invention is that, in the method for manufacturing the metal oxide powder, the first metal oxide particles and the second metal oxide particles are manufactured at the same time. Therefore, in the present embodiment, common parts with the first embodiment will not be described in an appropriate manner.

[Method for Manufacturing Metal Oxide Powder]

An example of a method for manufacturing the metal oxide powder according to the present embodiment will be described. In the following description, as the first metal oxide particles, star-like titanium oxide particles having an average primary particle diameter of 100 nm or more and 1,000 nm or less are used. In addition, as the second metal oxide particles, anatase-type granular titanium oxide particles having an average primary particle diameter of 1 nm or more and 40 nm or less are used.

The titanium oxide powder of the present embodiment can be manufactured by mixing a hydrolysis product of a titanium alkoxide or a titanium metal salt and an organic alkali so as to produce a reaction solution and reacting this reaction solution in the presence of high-temperature and high-pressure hot water (hydrothermal synthesis).

As the titanium alkoxide or the titanium metal salt in the present embodiment, the same titanium alkoxide or titanium metal salt as those that can be used in the first embodiment can be used. Therefore, the same hydrolysis product as that in the first embodiment is obtained.

The organic alkali in the present embodiment has a function as a pH adjuster for the reaction solution and a function as a catalyst for hydrothermal synthesis described below. Examples of the organic alkali include amines, high-molecular-weight amines, salts of high-molecular-weight amines, compounds having a five-membered ring including ammonia or nitrogen, and the like.

Examples of the amines include tetramethylammonium hydroxide, tetraethylammonium hydroxide, tetrapropylammonium hydroxide, tetrabutylammonium hydroxide, monoethanolamine, diethanolamine, triethanolamine, tetramethylammonium chloride, tetraethylammonium chloride, tetrapropylammonium chloride, tetrabutylammonium chloride, octylamine, laurylamine, stearylamine, and the like.

Examples of the high-molecular-weight amines and the salts of high-molecular-weight amines include high-molecular-weight amines and salts of high-molecular-weight amines which are made of the above-described amines.

As the compounds having a five-membered ring including nitrogen, the same compounds as those that can be used in the first embodiment can be used.

In the present embodiment, similar to the first embodiment, it is also possible to add water to the reaction solution and adjust the concentration of the reaction solution.

The pH of the solution after a hydrothermal reaction according to the present embodiment is preferably 9 to 11 and more preferably 9.5 to 10.5. In the embodiment, the pH of the solution after the hydrothermal reaction can be adjusted to the above-described range by controlling the amount of the organic alkali blended.

In the present embodiment, the shape, average primary particle diameter, and particle size distribution of titanium oxide particles being obtained can be controlled by adjusting the pH of the reaction solution.

The concentration of titanium atoms in the reaction solution according to the present embodiment can be appropriately set in accordance with the desired average primary particle diameter of titanium oxide particles. The concentration of the titanium atoms in the reaction solution is preferably 0.05 mol/L to 10 mol/L and more preferably 0.1 mol/L to 2.5 mol/L. In the present embodiment, the concentration of the titanium atoms in the reaction solution can be controlled in the above-described range by controlling the content of the hydrolysis product of the titanium alkoxide or the titanium metal salt.

When the concentration of titanium atoms in the reaction solution according to the present embodiment is in the above-described range, it is possible to control the average primary particle diameter of titanium oxide particles being obtained.

In the present embodiment, when the pH of the reaction solution and the concentration of titanium atoms are controlled to be in the above-described ranges, the reaction solution has a slurry form.

In the present embodiment, the amount of the compound having a five-membered ring including nitrogen blended is preferably 0.008 mol to 0.09 mol, more preferably 0.009 mol to 0.08 mol, and still more preferably 0.01 mol to 0.07 mol with respect to 1 mol of titanium atoms in the hydrolysis product.

In the present embodiment, when hydrothermal synthesis is carried out using the above-described reaction solution, the hydrolysis product of the titanium alkoxide or the hydrolysis product of the titanium metal salt in the reaction solution is decomposed at a high temperature and under pressure, and the crystal growth of the obtained titanium source progresses. In the hydrothermal synthesis in the present embodiment, similar to the first embodiment, a sealable high-temperature and high-pressure container (autoclave) is preferably used.

The heating temperature in the hydrothermal synthesis in the present embodiment is preferably 200° C. to 350° C., more preferably 210° C. to 350° C., and still more preferably 220° C. to 350° C. In the present embodiment, the heating rate from room temperature to the above-described temperature range is not particularly limited.

The heating time in the hydrothermal synthesis in the present embodiment is preferably two hours or longer and more preferably six hours to 12 hours.

In the hydrothermal synthesis in the present embodiment, it is preferable not to carry out preliminary heating (the pre-heating of the reaction solution at a temperature lower than the above-described temperature range). For example, when the preliminary heating is carried out in a temperature range of 70° C. to 150° C. for one hour or longer, only star-like titanium oxide particles having an average primary particle diameter of 100 nm or more and 1,000 nm or less are formed, and desired titanium oxide powder cannot be obtained. In contrast, when the preliminary heating is not carried out, titanium oxide particles having an average primary particle diameter of 1 nm or more and 40 nm or less as well as star-like titanium oxide particles having an average primary particle diameter of 100 nm or more and 1,000 nm or less are formed.

As a method for extracting the titanium oxide powder from the reaction solution and drying the titanium oxide powder, the same method as that in the first embodiment can be employed.

In the present embodiment, solutions including the hydrolysis product of the titanium alkoxide or the titanium metal salt or the reaction solution is preferably forcibly stirred using a stirring device such as a stirrer or a stirring blade. The stirring rate in the present embodiment is preferably, for example, 100 rpm to 300 rpm.

In the above-described manner, star-like titanium oxide particles having an average primary particle diameter of 100 nm or more and 1,000 nm or less and titanium oxide particles having an average primary particle diameter of 1 nm or more and 40 nm or less can be manufactured at the same time.

According to the present embodiment, it is possible to obtain metal oxide powder which has excellent light-scattering properties and provides dispersion liquids or cosmetic materials with excellent adhesiveness to substances to be coated when included in the dispersion liquids or the cosmetic materials. In the present embodiment, since the first metal oxide particles and the second metal oxide particles can be manufactured at the same time, it is easy to obtain metal oxide powder in which the first and second metal oxide particles are uniformly mixed together. Therefore, the dispersion liquid and the cosmetic material of the present embodiment have superior adhesiveness to substances to be coated to that of the dispersion liquid and the cosmetic material of the first embodiment.

EXAMPLES

Hereinafter, the present invention will be described in more detail using examples which do not limit the present invention. Addition, omission, substitution, and other modification of the constitution are allowed within the scope of the gist of the present invention.

In the present examples, as an example of metal oxide particles, titanium oxide particles were used.

<Production and Evaluation of Titanium Oxide Powder>
[Identification of Crystal Phase of Titanium Oxide Particles]

The crystal phase of the titanium oxide particles was identified using an X-ray diffraction device (manufactured by Spectris., X'Pert PRO)

[Identification of Principal Exposed Plane of Titanium Oxide Particles]

The principal exposed plane of the titanium oxide particle was identified using an FE-TEM (manufactured by JEOL Ltd., JEM-2100F). Specifically, the lattice image of the titanium oxide particles was observed using an FE-TEM, and the exposed crystal plane was determined from the plane spacing. At this time, in a case in which two or more principal exposed crystal planes were observed, the exposed surface was considered to be not determined.

[Measurement of Primary Particle Diameter and Average Primary Particle Diameter of Titanium Oxide Particles]

The primary particle diameters of the titanium oxide particles were measured using an image analysis device. As the primary particle diameter, a value at which the interval between two parallel lines between which individual metal oxide particles in a SEM image were inserted was maximized (the maximum Feret diameter (JIS Z 8827-1:2008)) was employed. A value obtained by randomly measuring 100 primary particle diameters and averaging the obtained measurement values in a weighted manner was used as the average primary particle diameter. In a case in which the titanium oxide particles formed agglomerates (secondary particles), the primary particle diameters of 100 randomly-selected primary particles constituting the secondary particles were measured, and the average primary particle diameter was obtained.

[Measurement of Masses of Titanium Oxide Particles and Particles Having Primary Particle Diameter of Less than 100 nm]

A method for measuring the mass of the titanium oxide particles will be described. First, the primary particle diameters (unit: nm) of 100 randomly-selected titanium oxide particles were measured on a SEM image. Next, the volume (unit: $nm^3$) of the titanium oxide particles was calculated from these primary particle diameters.

At this time, the volume of a star-like titanium oxide particle was obtained in the following manner.

First, when a star-like titanium oxide particle is divided along the crest lines and the trough lines between two crest lines using imaginary planes including the central axis Z, the star-like titanium oxide particle can be considered to be constituted of a collection of 12 triangular pyramids one of which is colored in the plan view of FIG. 1. Here, it is considered that the triangular pyramid which is a constituent unit has the right-side isosceles triangle obtained by dividing the cross-sectional view of FIG. 2 along the central axis Z as the basal plane.

In the case of being considered as described above, the height of the above-described triangular pyramid, crystallographically, reaches 0.142 times the primary particle diameter.

In addition, regarding the isosceles triangle which is the basal plane of the above-described triangular pyramid, the base of the isosceles triangle, crystallographically, reaches 0.563 times the primary particle diameter.

In addition, the height of the isosceles triangle, crystallographically, reaches 0.5 times the primary particle diameter.

When the volume of the triangular pyramid which is the above-described constituent unit is obtained from the above-described numerical values, and the obtained volume of the triangular pyramid is multiplied 12 times, the volume of the star-like titanium oxide particle can be approximately calculated. That is, the volume of the star-like titanium oxide particle can be obtained using Equation (1) below. In the present examples, the volume of the star-like titanium oxide particle was calculated on the basis of Equation (1) below.

$$\text{Volume of star-like titanium oxide particle} = 0.08 \times (\text{primary particle diameter})^3 \quad (1)$$

In addition, in a case in which it is possible to approximate the shape of the titanium oxide particle to a sphere, the volume of the titanium oxide particle was calculated on the basis of an equation for obtaining the volume of the sphere. The mass of the titanium oxide particle was calculated by multiplying this volume by the density of the titanium oxide particle.

[Measurement of Content of Titanium Oxide Particles]

The content of the titanium oxide particles with respect to the mass of the titanium oxide powder was measured using a high-frequency ICP emission spectrometer (manufactured by Rigaku Corporation, CIROS-120 EOP).

Manufacturing Example 1

(Hydrolysis)

Pure water (250 mL) cooled to 10° C. was put into a glass container having a capacity of 1 L, and titanium tetraisopropoxide (manufactured by Kojundo Chemical Lab. Co., Ltd.) (71 g) was added dropwise to this pure water using a dropping funnel under stirring at 300 rpm with a stirring blade and was reacted for one hour. Therefore, a white water-based suspension including a hydrolysis product of titanium tetraisopropoxide was obtained. This water-based suspension was suction-filtered using a Nutsche filter and filter paper (manufactured by Toyo Roshi International, Inc., No 2), thereby obtaining a hydrolysis product of titanium tetraisopropoxide as a white cake-form solid. This cake-form solid was cleaned with pure water (500 mL).

(Preparation of Reaction Solution)

The cleaned hydrolysis product of titanium tetraisopropoxide and an aqueous solution of 26% tetramethylammonium hydroxide (manufactured by Tokyo Chemical Industry Co., Ltd.) (1.4 g) were put into pure water, thereby preparing a reaction solution so that the total mass reached 200 g. It was confirmed that the concentration of titanium atoms in the reaction solution was 1.25 mol/L.

(Hydrothermal Synthesis)

The above-described reaction solution was put into an autoclave and was pre-heated at 120° C. for four hours. After that, the reaction solution was heated at 270° C. for 12 hours and was reacted, thereby obtaining a white water-based suspension including titanium oxide particles. This water-based suspension was suction-filtered using a Nutsche filter and filter paper (manufactured by Toyo Roshi International, Inc., No 2), thereby obtaining a white cake-form solid including titanium oxide particles. This cake-form solid was cleaned with pure water (500 mL) and was dried at 120° C. one night, thereby obtaining titanium oxide particles of Manufacturing Example 1.

It was found that the titanium oxide particles of Manufacturing Example 1 were star-like titanium oxide particles having an average primary particle diameter of 300 nm. It was found that these titanium oxide particles were anatase-type star-like titanium oxide particles, in which a principal exposed crystal plane is a (101) plane.

Manufacturing Example 2

(Hydrolysis)

Pure water (1 L) cooled to 10° C. was put into a glass container having a capacity of 2 L. Titanium tetraisopropoxide (manufactured by Kojundo Chemical Lab. Co., Ltd.) (71 g) was added dropwise to this pure water using a dropping funnel under stirring at 300 rpm with a stirring blade and was reacted for one hour. Therefore, a white water-based suspension including a hydrolysis product of titanium tetraisopropoxide was obtained. This water-based suspension was suction-filtered using a Nutsche filter and filter paper (manufactured by Toyo Roshi International, Inc., No 2), thereby obtaining a hydrolysis product of titanium tetraisopropoxide as a white cake-form solid. This cake-form solid was cleaned with pure water (500 mL).

(Preparation of Reaction Solution)

The cleaned hydrolysis product of titanium tetraisopropoxide and pyrrolidine (manufactured by Kanto Kagaku) (2.5 g) were put into pure water, thereby preparing a reaction solution so that the total mass reached 1 kg. In addition, it was confirmed that the concentration of titanium atoms in the reaction solution was 0.25 mol/L.

(Hydrothermal Synthesis)

The above-described reaction solution was put into an autoclave, was heated at 200° C. for nine hours, and was reacted, thereby obtaining a white water-based suspension including titanium oxide particles. This water-based suspension was suction-filtered using a Nutsche filter and filter paper (manufactured by Toyo Roshi International, Inc., No 2), thereby obtaining a white cake-form solid including titanium oxide particles. This cake-form solid was cleaned with pure water (500 mL) and was dried at 120° C. one night, thereby obtaining titanium oxide particles of Manufacturing Example 2.

It was found that the titanium oxide particles of Manufacturing Example 2 were anatase-type granular titanium oxide particles, in which a principal exposed crystal plane is a (101) plane. It was found that the average primary particle diameter of these titanium oxide particles was 20 nm.

Manufacturing Example 3

Titanium oxide particles of Manufacturing Example 3 were obtained in the same manner as in Manufacturing Example 1 except for the fact that the reaction solution was heated at 250° C. for eight hours without being pre-heated.

It was found that the titanium oxide particles of Manufacturing Example 3 included titanium oxide particles, in which a principal exposed crystal plane is a (101) plane. In addition, it was found that the titanium oxide particles included star-like titanium oxide particles having an average primary particle diameter of 300 nm and granular titanium oxide particles having an average primary particle diameter of 20 nm.

Table 1 shows the shapes, average primary particle diameters, crystal phases, and principal exposed crystal planes of the titanium oxide particles manufactured in Manufacturing Examples 1 to 3.

TABLE 1

| | Shape | Average primary particle diameter (nm) | Crystal phase | Principal exposed crystal plane |
|---|---|---|---|---|
| Manufacturing Example 1 | Star-like | 300 | Anatase single-phase | (101) plane |
| Manufacturing Example 2 | Granular | 20 | Anatase single-phase | (101) plane |
| Manufacturing Example 3 | Star-like | 300 | Anatase single-phase | (101) plane |
| | Granular | 20 | Anatase single-phase | (101) plane |

Example 1

The star-like titanium oxide particles (1.99 g) produced in Manufacturing Example 1 and the anatase-type granular titanium oxide particles (0.01 g) produced in Manufacturing Example 2 were mixed together using a mortar, thereby obtaining titanium oxide powder of Example 1.

It was found that the obtained titanium oxide powder included 0.5% by mass of particles which had a primary particle diameter of less than 100 nm of the total mass of the titanium oxide powder. It was found that this titanium oxide powder included 99.9% by mass of the star-like titanium oxide particles and the anatase-type granular titanium oxide particles of the total mass of the titanium oxide powder. That is, it was confirmed that the titanium oxide powder substantially did not include any components other than the titanium oxide particles and high-purity titanium oxide particles were obtained.

Example 2

The star-like titanium oxide particles (1.84 g) produced in Manufacturing Example 1 and the anatase-type granular titanium oxide particles (0.16 g) produced in Manufacturing Example 2 were mixed together using a mortar, thereby obtaining titanium oxide powder of Example 2.

It was found that the obtained titanium oxide powder included 8% by mass of particles which had a primary particle diameter of less than 100 nm of the total mass of the titanium oxide powder. It was found that this titanium oxide powder included 99.9% by mass of the star-like titanium oxide particles and the anatase-type granular titanium oxide particles of the total mass of the titanium oxide powder.

Example 3

The star-like titanium oxide particles (1.96 g) produced in Manufacturing Example 1 and the anatase-type granular titanium oxide particles (0.04 g) produced in Manufacturing Example 2 were mixed together using a mortar, thereby obtaining titanium oxide powder of Example 3.

It was found that the obtained titanium oxide powder included 2% by mass of particles which had a primary particle diameter of less than 100 nm of the total mass of the titanium oxide powder. Furthermore, it was found that this titanium oxide powder included 99.9% by mass of the star-like titanium oxide particles and the anatase-type granular titanium oxide particles of the total mass of the titanium oxide powder.

Example 4

Figure 4:
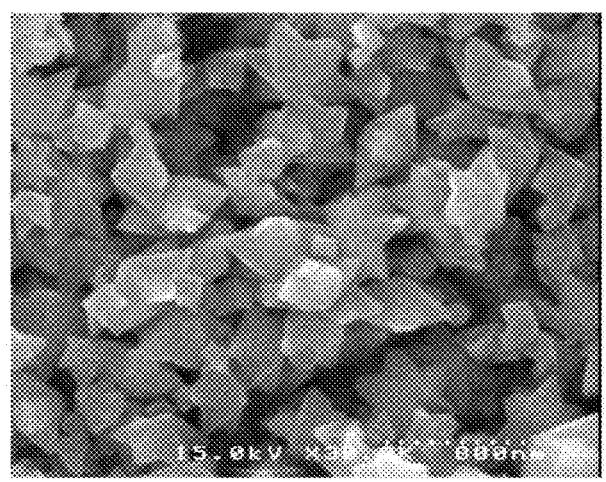
FIG. 4 is a scanning electron microscopic image illustrating titanium oxide powder of Example 4.

Titanium oxide powder of Example 4 was obtained using the titanium oxide particles (2 g) produced in Manufacturing Example 3. FIG. 4 illustrates a SEM image of the titanium oxide powder according to Example 4. It was found that the obtained titanium oxide powder included 1.5% by mass of particles which had a primary particle diameter of less than 100 nm of the total mass of the titanium oxide particles. In addition, it was found that the titanium oxide powder included 0.2% by mass of star-like titanium oxide particles which were smaller than 100 nm of the total mass of the particles which had a primary particle diameter of less than 100 nm. It was found that these titanium oxide powder included 99.9% by mass of the star-like titanium oxide particles and the anatase-type granular titanium oxide particles of the total mass of the titanium oxide powder.

Comparative Example 1

Figure 5:
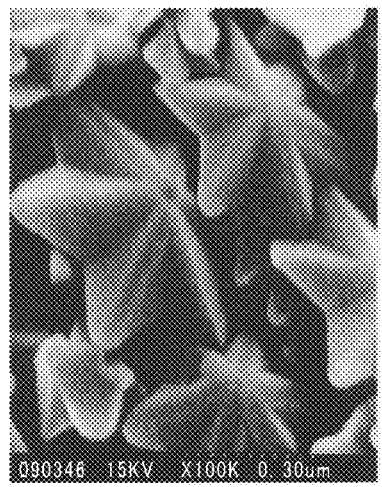
FIG. 5 is a scanning electron microscopic image illustrating titanium oxide powder of Comparative Example 1.

Titanium oxide powder of Comparative Example 1 was obtained using the star-like titanium oxide particles (2 g) produced in Manufacturing Example 1. FIG. 5 illustrates a SEM image of the titanium oxide powder according to Comparative Example 1. The obtained titanium oxide powder did not include any particles having a primary particle diameter of less than 100 nm.

Comparative Example 2

Figure 6:
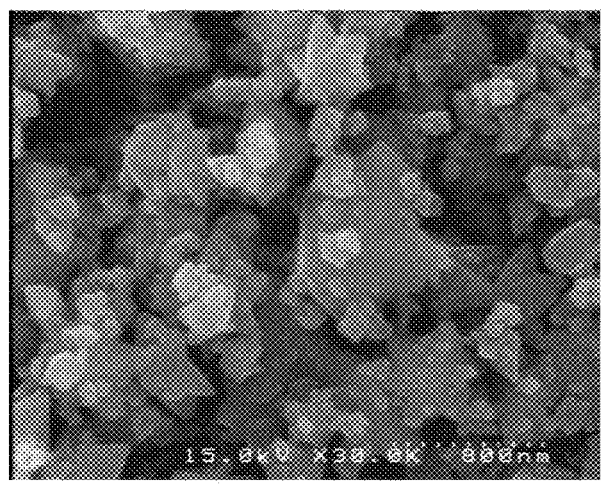
FIG. 6 is a scanning electron microscopic image illustrating titanium oxide powder of Comparative Example 2.

The star-like titanium oxide particles (1.6 g) produced in Manufacturing Example 1 and the anatase-type granular titanium oxide particles (0.4 g) produced in Manufacturing Example 2 were mixed together using a mortar, thereby obtaining titanium oxide powder of Comparative Example 2. FIG. 6 illustrates a SEM image of the titanium oxide powder according to Comparative Example 2. It was found that the obtained titanium oxide powder included 20% by mass of particles which had a primary particle diameter of less than 100 nm of the total mass of the titanium oxide powder.

<Production and Evaluation of Cosmetic Materials>

Titanium oxide powder and talc, which has been used as a vehicle for foundation in the related art, were mixed together, thereby producing pseudo foundation. Specifically, the titanium oxide powder (2 g) of each of the examples and the comparative examples and talc (8 g) were mixed together using a mortar, thereby obtaining powder for evaluation.

The obtained powder for evaluation was placed on a 50 mm×50 mm substrate (manufactured by HelioScreen, helioplate HD-6) so that the film thickness reached 3 μm, thereby producing an evaluation sample.

[Evaluation of Light-Scattering Properties]

The integral reflectivity of the obtained evaluation sample at 450 nm, 600 nm, and 750 nm was measured, thereby evaluating the light-scattering properties of the titanium oxide powder of Examples 1 to 4 and Comparative Examples 1 and 2. The integral reflectivity of the evaluation sample was measured using an ultraviolet and visible spectrophotometer (manufactured by Shimadzu Corporation, UV-3150). As a reference sample having an integral reflectivity of 100%, a green compact of barium sulfate (manufactured by Kanto Chemical Co., Inc.) was used.

[Evaluation of Adhesiveness]

Tape for adhesiveness test (manufactured by Nichiban Co., Ltd., CT-12, 50 mm×12 mm) was attached to the obtained evaluation sample, was slowly peeled off, and the mass (A) of the evaluation sample was measured. The peeling percentages of the titanium oxide powder of Examples 1 to 3 were calculated on the basis of Equation (2) below using the previously-measured mass (B) of the substrate and the mass (C) of the evaluation sample.

$$\text{Peeling percentage } (\%) = 100 \times (C-A)/(C-B) \quad (2)$$

Table 2 shows the evaluation results of the light-scattering properties and adhesiveness of the titanium oxide powder produced in the examples and the comparative examples.

TABLE 2

| | First metal oxide particles | Second metal oxide particles | Content of particles having primary particle diameter of less than 100 nm (% by mass) | Integral reflectivity (%) | | | Peeling percentage (%) |
|---|---|---|---|---|---|---|---|
| | | | | 450 nm | 600 nm | 750 nm | |
| Example 1 | Manufacturing Example 1 | Manufacturing Example 2 | 0.5 | 48 | 45 | 42 | 10.8 |
| Example 2 | Manufacturing Example 1 | Manufacturing Example 2 | 8 | 46 | 43 | 40 | 8.6 |
| Example 3 | Manufacturing Example 1 | Manufacturing Example 2 | 2 | 47 | 45 | 40 | 9.1 |
| Example 4 | Manufacturing Example 3 | | 1.5 | 47 | 44 | 40 | 7.8 |
| Comparative Example 1 | Manufacturing Example 1 | Not included | Not included | 51 | 49 | 47 | 13.2 |
| Comparative Example 2 | Manufacturing Example 1 | Manufacturing Example 2 | 20 | 37 | 32 | 19 | 6.7 |

It was found that, in the present examples, the titanium oxide powder of the present invention had excellent light-scattering properties. Specifically, it was found that the powder for evaluation of Examples 1 to 4 had a higher integral reflectivity at all measurement wavelengths and better light-scattering properties than the powder for evaluation of Comparative Example 2.

In addition, it was found that the powder for evaluation obtained by mixing the titanium oxide powder of the present invention and talc had excellent adhesiveness to substrates. Specifically, the powder for evaluation of Examples 1 to 4 had a lower peeling percentage and better adhesiveness to substrates than the powder for evaluation of Comparative Example 1.

As described above, it was found that cosmetic materials to which the titanium oxide powder of the present invention is added are excellent in terms of both light-scattering properties and adhesiveness to substrates. Therefore, cosmetic materials to which the titanium oxide powder of the present invention is added are considered to be excellent in terms of opacifying power and makeup-lasting properties.

INDUSTRIAL APPLICABILITY

It is possible to provide metal oxide powder which has excellent light-scattering properties and has excellent adhesiveness when included in dispersion liquids and cosmetic materials, a dispersion liquid, and a cosmetic material.

REFERENCE SIGNS LIST

1 First protrusion portion
2 Second protrusion portion
1a Tip of first protrusion portion
2a Tip of second protrusion portion
10 Crest
100, 101 First metal oxide particle
Z Central axis

The invention claimed is:

1. Metal oxide powder formed of metal oxide particles, consisting of:
    a first metal oxide particle that has at least one protrusion portion and a second metal oxide particle,
    wherein the first metal oxide particles have an average primary particle diameter of 100 nm or more and 1,000 nm or less, and the material forming the first metal oxide particles is anatase-type titanium oxide,
    the second metal oxide particles have an average primary particle diameter of less than 100 nm, and the material forming the second metal oxide particles is anatase-type titanium oxide, and,
    a fraction of a total mass of particles having a primary particle diameter of less than 100 nm in a total mass of the metal oxide powder is 0.3% by mass or more and 10% by mass or less.

2. The metal oxide powder according to claim 1, wherein the first metal oxide particle includes
    a plurality of first protrusion portions radially protruding from a central axis of the first metal oxide particle in substantially perpendicular directions, and
    a pair of second protrusion portions protruding in a direction in which tips are away from each other along the central axis,
    has a crest formed between a tip of the first protrusion portion and the tip of the second protrusion portion, and
    has a star-like shape as a whole.

3. The metal oxide powder according to claim 1, wherein the fraction of the total mass of the first metal oxide particles in the total mass of the metal oxide powder is 90% by mass or more and 99.7% by mass or less.

4. Metal oxide powder consisting of:
    a first metal oxide particle that has at least one protrusion portion, a second metal oxide particle, and a surface-treated layer formed of a surface treatment agent on a surface of the metal oxide particle,
    wherein the first metal oxide particles have an average primary particle diameter of 100 nm or more and 1,000 nm or less, and the material forming the first metal oxide particles is anatase-type titanium oxide,
    the second metal oxide particles have an average primary particle diameter of less than 100 nm, and the material forming the second metal oxide particles is anatase-type titanium oxide,
    a fraction of a total mass of particles having a primary particle diameter of less than 100 nm in a total mass of the metal oxide powder is 0.3% by mass or more and 10% by mass or less, and
    the surface treatment agent is at least one selected from the group consisting of silica, alumina, silicone compounds, organopolysiloxanes, fatty acids, fatty acid soap, fatty acid esters, organic titanate compounds, and a surfactant.

5. Metal oxide powder formed of metal oxide particles,
    wherein the metal oxide powder has first metal oxide particles having at least one protrusion portion and second metal oxide particles,
    the first metal oxide particles have an average primary particle diameter of 100 nm or more and 1,000 nm or less,
    the second metal oxide particles have an average primary particle diameter of less than 100 nm, and
    a fraction of a total mass of particles having a primary particle diameter of less than 100 nm in a total mass of the metal oxide powder is 0.3% by mass or more and 10% by mass or less,
    wherein the metal oxide powder has 46-48% integral reflectivity at 450 nm, 43-45% reflectivity at 600 nm, 40-42% reflectivity at 750 nm, and
wherein the metal oxide powder has a peeling percentage of 7.8-10.8%.

6. A dispersion liquid formed by the method comprising the steps of:
    combining (i) a metal oxide powder wherein the metal oxide powder has a first metal oxide particle that has at least one protrusion portion and a second metal oxide particles, and (ii) a liquid dispersion medium, thereby forming the dispersion liquid,
    wherein the first metal oxide particles have an average primary particle diameter of 100 nm or more and 1,000 nm or less,
    the second metal oxide particles have an average primary particle diameter of less than 100 nm,
    a fraction of a total mass of particles having a primary particle diameter of less than 100 nm in a total mass of the metal oxide powder is 0.3% by mass or more and 10% by mass or less,
    the metal oxide powder has 46-48% integral reflectivity at 450 nm, 43-45% reflectivity at 600 nm, 40-42% reflectivity at 750 nm, and
    the metal oxide powder has a peeling percentage of 7.8-10.8%.

7. A cosmetic material formed by the method comprising the steps of:
    combining (i) a metal oxide powder wherein the metal oxide powder has a first metal oxide particles that has at least one protrusion portion and a second metal oxide particle, and (ii) a cosmetic vehicle raw material, thereby forming the cosmetic material,
    wherein the first metal oxide particles have an average primary particle diameter of 100 nm or more and 1,000 nm or less,
    the second metal oxide particles have an average primary particle diameter of less than 100 nm,
    a fraction of a total mass of particles having a primary particle diameter of less than 100 nm in a total mass of the metal oxide powder is 0.3% by mass or more and 10% by mass or less, the metal oxide powder has 46-48% integral reflectivity at 450 nm, 43-45% reflectivity at 600 nm, 40-42% reflectivity at 750 nm, and the metal oxide powder has a peeling percentage of 7.8-10.8%.

* * * * *